United States Patent [19]

Connor et al.

[11] Patent Number: 4,675,332

[45] Date of Patent: Jun. 23, 1987

[54] ACIDIC TETRAZOLYL SUBSTITUTED INDOLE COMPOUNDS AND THEIR USE AS ANTIALLERGY AGENTS

[75] Inventors: David T. Connor; Paul C. Unangst; S. Russell Stabler, all of Ann Arbor, Mich.

[73] Assignee: Warner-Lambert Company, Morris Plains, N.J.

[21] Appl. No.: 788,111

[22] Filed: Oct. 21, 1985

Related U.S. Application Data

[63] Continuation-in-part of Ser. No. 680,116, Dec. 10, 1984, abandoned.

[51] Int. Cl.[4] .................... C07D 403/12; C07D 403/4; A61K 31/41
[52] U.S. Cl. .................... 514/381; 548/253; 548/251
[58] Field of Search ............... 548/251, 253; 514/381

[56] References Cited

U.S. PATENT DOCUMENTS 3,417,096 12/1968 Juby ..................................... 548/253
4,316,904 2/1982 Brown et al. ...................... 548/253
4,581,354 4/1986 Bell ..................................... 548/493

FOREIGN PATENT DOCUMENTS 80371 11/1981 European Pat. Off. ............ 548/252
71935 2/1983 European Pat. Off. .

OTHER PUBLICATIONS

B. Samuelsson, "Leukotrienes: Mediators of Immediate Hypersensitivity Reactions and Inflammation," *Science*, vol. 220, pp. 568 (1983).
P. J. Piper, "Leukotrienes," *Trends in Pharmacological Sciences*, pp. 75 & 77 (1983).
J. L. Romson, et al; "Reduction of the Extent of Ischemic Myocardial Injury by Neutrophil Depletion in the Dog," *Circulation*, vol. 67, p. 1016 (1983).
Official Gazette, Jan. 6, 1987, p. 436.

*Primary Examiner*—Richard L. Raymond
*Assistant Examiner*—D. B. Springer
*Attorney, Agent, or Firm*—Joan Thierstein

[57] ABSTRACT

Novel acidic indole compounds having use as antiallergic agents, methods of synthesis, compositions, and uses are claimed.

29 Claims, No Drawings

ACIDIC TETRAZOLYL SUBSTITUTED INDOLE COMPOUNDS AND THEIR USE AS ANTIALLERGY AGENTS

This application is a continuation-in-part of U.S. Ser. No. 680,116, filed Dec. 10, 1984, now abandoned.

BACKGROUND OF THE INVENTION

The present invention provides novel acidic indole compounds, novel methods for synthesis thereof, selected novel intermediates, pharmaceutical compositions and uses of the novel compounds, particularly as antiallergic agents. Additionally, the compounds prevent the release of mediators such as leukotrienes from basophils and neutrophils providing activity useful in cardiovascular disorders as well as in antiinflammatory and antimigraine treatment. See B. Samuelsson, "Leukotrienes: Mediators of Immediate Hypersensitivity Reactions and Inflammation," *Science*, Vol. 220, pp 568 (1983), P. J. Piper, "Leukotrienes," *Trends in Pharmacological Sciences*, pp 75 & 77 (1983), and J. L. Romson, et al; "Reduction of the Extent of Ischemic Myocardial Injury by Neutrophil Depletion in the Dog," *Circulation*, Vol. 67, p 1016 (1983).

European Patent Application No. 71,935 discloses indole derivatives. However, the novel compounds of the present invention include differences from the compounds in EP No. 71,935 not suggested by its disclosure.

Furthermore, the antiallergic utility now found for the novel compounds of the present invention is not within the teachings for the indole derivatives disclosed by the EP No. 71,935 reference.

SUMMARY OF THE INVENTION

The present invention is a compound of Formula I,

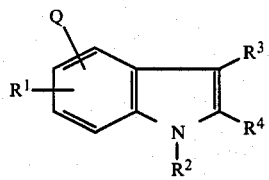

wherein (1) $R^1$ and Q are independently H, alkyl of from one to twelve carbons, inclusive, alkoxy of from one to twelve carbons, inclusive, mercapto, alkylthio of from one to four carbons, inclusive, alkylsulfinyl of from one to four carbons, inclusive, alkylsulfonyl of from one to four carbons, inclusive, hydroxy, $R^1$ taken twice having each on adjacent carbons such that the two $R^1$s together are methylenedioxy, nitro, amino, substituted amino, or halogen; (2) $R^2$ is H, alkyl of from one to twelve carbons, inclusive, phenyl, substituted phenyl, or benzyl; (3) $R^3$ is H, alkyl of from one to twelve carbons, inclusive, alkoxy of from one to twelve carbons, inclusive, mercapto, alkylthio of from one to four carbons, inclusive, phenylthio, substituted phenylthio, alkylsulfinyl of from one to four carbons, inclusive, phenylsulfinyl, substituted phenylsulfinyl, alkylsulfonyl of from one to four carbons, inclusive, phenylsulfonyl, substituted phenyl sulfonyl, amino, and substituted amino; and (4) $R^4$ is A or B; and pharmaceutically acceptable salts thereof.

Further, the present invention includes a process for the preparation of a compound of Formula I, wherein $R^1$, Q, $R^2$, $R^3$, and $R^4$ are as defined above, which comprises treating a compound having the Formula III, wherein $R^1$, Q, $R^2$, and $R^3$ are as defined above to obtain the compound of Formula I as shown in Scheme I.

The process which comprises treating the compound of Formula III to obtain the compound of Formula $I_1$, wherein $R^4$ of Formula I is the moiety shown by A comprises contacting the compound of Formula III with the compound of Formula II, in the presence of a coupling agent. See Scheme II.

A compound of Formula III is known or can readily be prepared from compounds known in the literature. For example, compounds of Formula III wherein $R^3$ is an amino or a substituted amino may be prepared in a manner analogous to or derived from the process described by P. C. Unangst, *J. Heterocyclic Chem.*, Vol. 20, 495 (1983). Unangst describes compounds in which the substituent is an amino. Substituted amino groups can be prepared from the amino compounds by standard methods.

An alternate route to compounds of Formula III having $R^3$ as amino or substituted amino groups may be analogous to a reaction described by M. A. Khan, et al, in *Chem. Pharm. Bull.*, Vol. 25, 3110 (1977).

Compounds of Formula III wherein $R^3$ is a mercapto or alkylthio within the present invention is shown or can be made by procedures from analogous compounds to those shown by K. Nagarajan, et al, *Indian J. of Chem.*, Vol. 20B, 672 (1981). Likewise, compounds of Formula III wherein $R^3$ is alkylsulfinyl or alkylsulfonyl can be prepared by oxidation of the corresponding alkylthio compounds by methods familiar to those skilled in the art.

The process which comprises treating the compound of Formula III to obtain the compound of Formula $I_2$ wherein $R^4$ of Formula I is the moiety shown by B is one in which the compound of Formula III is (1) contacted with ammonia and the resulting amide dehydrated to give a compound of Formula IV, wherein $R^1$, Q, $R^2$, and $R^3$ are as defined above and (2) the compound of Formula IV is then treated in a manner analogous to that described by the K. Sisido cited reference hereinafter to give the compound of Formula Formula $I_2$. See Scheme III.

Additionally, the present invention includes a process for the preparation of the compound of Formula $I_3$ wherein $R^1$, Q, and $R^2$ are as defined above and $OR^6$ wherein $R^6$ is benzyl or alkyl of from one to twelve carbons, inclusive, which comprises (1) esterifying a compound of Formula VII (2) treating the esterification product to obtain a compound of Formula VI by a reaction analogous to that described by K. Sisido, et al, *J. Organometallic Chem.*, Vol. 33, 337 (1971), protecting the compound of Formula VI wherein Y is an appropriate protecting group, and cyclizing the protected compound, and finally, alkylating with a compound $HalR^6$, wherein $R^6$ is as defined above, and then deprotecting to obtain the compound $I_3$. Cyclization is accomplished generally by treating the protected compound of Formula VI with potassium butoxide in tetrahydrofuran. See Scheme IV. Cyclization can also be used to prepare a compound of Formula IV of Scheme III for use as an intermediate in the preparation of compounds of Formula $I_3$ described above. For example, esterification of a compound of Formula VIII, wherein $R^1$ and $R^2$ are as defined above may be followed by cyclization to obtain the compound IV. See Scheme V.

The antiallergy activity of the compounds having the Formula I of the present invention was determined by the well-known Schultz-Dale procedure, that is described in N. Chand, et al, *Agents and Actions,* Vol. 8, 171 (1978), or the Herxheimer in vivo antiallergy test, described in H. Herxheimer, *J. Physiol. (London)* Vol. 117, 251 (1952).

By virtue of this antiallergy activity the compounds of Formula I are useful in treating an allergic hypersensitivity reaction (AHR) having broad symptoms. For example, the symptoms may include dermatitis, lacrimation, nasal discharge, coughing, sneezing, nausea, vomiting, diarrhea, difficulty in breathing, pain, inflammation, and in severe cases, anaphylactic shock, circulatory collapse, and even death. The AHR is found in man as well as other animals suffering from bronchial asthma, seasonal pollinosis (e.g., hayfever), allergic rhinitis, urticoria, allergic conjunctivitis, food allergies, and anaphylactoid reactions.

In an AHR an antibody (reagin in man) influences the cell membrane of a mast cell by reacting with an antigen, to initiate reactions within the mast cell which ultimately causes release of mediators (bioactive compounds) such as bradykinin, slow reacting substance A (SRS-A), histamine, serotonin (5HT), possibly some prostaglandins, or other not now known substances. The mediator is released from the mast cell whereupon it attaches to suitable receptor sites (e.g., on smooth muscle) resulting in AHR attack symptoms. Various methods are used to relieve the symptoms of AHR. It is not known, however, what mechanism is effected for the antiallergic use by the compounds having Formula I of the present inventions.

Pharmaceutical compositions are prepared from compound Formula I and salts thereof described as the present invention having inert pharmaceutical carriers. The compositions may be either solid or liquid.

A physician or veterinarian of ordinary skill readily determines a subject who is exhibiting AHR symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area, (e.g., in the form of eye drops or by inhalation). For the treatment of AHR induced conditions such as erythema, the compounds of the present invention may also be administered topically in the form of ointments, creams, gels, or the like. In general, the preferred route of administration is orally.

An effective but nontoxic quantity of the compound is employed in treatment. The ordinarily skilled physician or veterinarian will readily determine and prescribe the effective amount of the anti-AHR agent to prevent or arrest the progress of the condition. In so proceeding, the physician or veterinarian could employ relatively low dosages at first, subsequently increasing the dose until a maximum response is obtained.

Initial dosages of the compounds of the invention having Formula I are ordinarily in the area of 10 mg up to 2 g per day orally, preferably 10 mg to 500 mg per dose orally, given from one to four times daily or as needed. When other forms of administration are employed equivalent doses are administered.

The compounds of this invention can also be administered as pharmacologically acceptable salts such as can be readily prepared with inorganic and organic bases, such as NaOH, KOH, $Mg(OH_2)$, $Ca(OH)_2$, $NH_4OH$, substituted ammonium salts, L-arginine, choline, N-methyl glucamine and the like.

The novel compounds of Formula I are named as derivatives of indoles by virtue of a nitrogen containing heterocyclic five-membered ring fused to a phenyl ring. The fused rings are numbered counterclockwise starting with the nitrogen atom at the one position as shown in the ring system of Formula I'.

Certain compounds within the scope of Formula I are preferred, since they have a more advantageous pharmacologic effect. Preferred compounds include compounds of Formula I wherein Q is hydrogen. Compounds of the Formula I more preferred are the following compounds: (1) 5-methoxy-3-(1-methylethoxy)-1-phenyl-N-1H-tetrazol-5-yl-1H-indole-2-carboxamide, and (2) 3-ethoxy-5-methoxy-1-phenyl-N-1H-terazol-5-yl-1H-indole-2-carboxamide.

Of the above, the most preferred compound is 5-methoxy-3-(1-methylethoxy)-1-phenyl-N-1H-tetrazol-5-yl-1H-indole-2-carboxamide.

Alkyl of from one to four carbons, inclusive, is methyl, ethyl, propyl, butyl, or isomeric forms thereof.

Alkyl of from one to twelve carbons, inclusive, is methyl, ethyl, propyl, butyl, pentyl, hexyl, heptyl, octyl, nonyl, etc, and includes isomeric forms of the alkyl of from one to six carbons, inclusive. Alkyl of from one to six carbons, inclusive, are preferred.

Alkoxy of from one to twelve carbons, inclusive, is methoxy, ethoxy, propoxy, butoxy, etc, and includes isomeric forms of alkoxy of from one to six carbons, inclusive. Alkoxy of from one to six carbons, inclusive, are preferred.

Substituted phenyl is a phenyl having at least one substituent and particularly one or two substituents such as, alkyl of from one to four carbons, inclusive, alkoxy of from one to four carbons, inclusive, hydroxy, nitro, amino, substituted amino, mercapto, alkylthio of from one to four carbons, methylenedioxy, or halogen.

Substituted amino or mono- or di-alkyl amino wherein alkyl is from one to four carbons, inclusive.

Halogen is fluoro, chloro, bromo, iodo, or trifluoromethyl.

The compounds of this invention are synthesized as illustrated in Schemes I–V.

Generally, the compounds having the Formula I, as illustrated in Scheme I are prepared by treating an indole-2-carboxylic acid of Formula III wherein $R^1$, Q, $R^2$, and $R^3$ are as defined above.

A 3-alkoxy ester of Formula IX, wherein $R^1$, Q, and $R^2$ are as defined above, $R^3$ is alkoxy, and $R^5$ is benzyl or alkyl of from one to six, inclusive, as shown in Scheme VI may be prepared by methods analogous to those known in the literature. See for example, H. Plieninger, et al, *Chem. Ber.,* Vol. 104, 1863 (1971), and J. Galun, et al, *J. Heterocyclic Chem.,* Vol. 16, 221 (1979). If $R^3$ is hydroxy in the compound of Formula IX it must be prepared by, for example, treatment with a compound of Formula $R^6X$ wherein $R^6$ is alkyl of from one to six carbons, inclusive, or benzyl and X is halogen, sulfonate or the like using conditions analogous to those known in the art. Protection of other $R^1$, Q, $R^2$, or $R^3$ groups is also readily understood by those skilled in the art.

The 3-alkoxy ester is then converted to carboxylic acids of Formula III wherein $R^1$, Q, and $R^2$, are as defined above, and $R^3$ is alkoxy.

The conversion is accomplished using standard conditions, such as, using either a strong base, NaOH, KOH, and the like, or analogous organic bases such as, potassium tertiary-butoxide, or the like followed by acidification. (see a similar process in indole chemistry in the A. Galun, et al, reference cited above).

Additionally, the general preparation of a compound of Formula I wherein $R^4$ is A, $R^3$ is amino or substituted amino and $R^1$, Q, and $R^2$ are as defined above may also be accomplished as shown in Scheme VII. That is, a mixture of a compound of Formula XX wherein $R^1$, Q, and $R^2$ are as defined above and an alkylaldehyde of from one to four carbons, inclusive in a solvent such as tetrahydrofuran, acetonitrile or the like, is treated with sodium cyanoborohydride. The resulting compound of Formula XXI wherein $R^7$ and $R^8$ are independently hydrogen or alkyl of from one to four carbons, inclusive, and $R^1$ and Q are as defined above is then reacted with $R^2$ Cl or $R^2$ Br wherein $R^2$ is as defined above to obtain the compound of Formula IX. Such a compound of Formula IX, wherein $R^1$, Q, $R^2$ and $R^7$ and $R^8$ are as defined above may be directly coupled with the compound of Formula II in the presence of lithium diisopropylamine or treated as shown in Scheme VI and further, optionally treated as for Schemes I, II or III as described above.

A compound of Formula XX wherein $R^1$ is 5-methoxy and Q is hydrogen is known and is prepared by the procedure described in S. V. Simakov, et al, *Khim-Farm. Zh.*, 17, p. 1183 (1983). Other definitions for $R^1$ and Q in the compound of Formula XX may be prepared by analogues procedures.

The preparation of XXI is generally conducted by the procedures known as reductive amination and the further reaction to convert the compound of Formula XXI to the compound of Formula $IX_1$, is analogous to the reaction having conditions known as an Ullmann reaction.

Also, the compound of Formula I wherein $R^4$ is A, and $R^3$ is alkylthio or alkylsulfonyl may be prepared by the processes shown in Scheme VIII. The compounds of Formula XXX wherein $R^1$ and Q are as defined above are prepared by known methods, methods analogous to known methods or are commercially available and are reacted with $R^2$ Br or $R^2$Cl wherein $R^2$ is as defined above using conditions analogous to those described as an Ullmann reaction and shown as step 2 of Scheme VIII. Then the carboxylic acid group is protected, for example, by reaction with $CH_3I$ to form an ester of Formula XXXII wherein $R^1$, Q, and $R^2$ are as defined above and then treated with thionyl chloride in a reaction similar to that described by J. Szmuszkovicz, *J. Org. Chem.*, 29, p 178 (1964) to obtain the sulfinyl chloride of Formula XXXIII wherein $R^1$, Q, and $R^2$ are as defined above.

The compound of Formula XXXIII reacts with a Grignard reagent or an alkyl cuprate reagent to yield alkylsulfinyl or phenyl- or substituted phenylsulfinylindoles of the Formula XXXIV wherein $R^9$ is alkyl of from one to four carbons, inclusive, phenyl or substituted phenyl. The sulfinyl indoles of Formula XXXIV may then be reduced with trifluoroacetic anhydride and sodium iodide to provide the compound of Formula IX, or further reacted to give the compound of Formula $IX_3$. Again the Formula IX may be coupled with 5-aminotetrazol by various procedures discussed above to give a compound of Formula I wherein $R^3$ is $SR^9$ wherein $R^9$ is as defined above and $R^1$, Q, and $R^2$ are also as defined above. A compound of Formula I wherein $R^3$ is $SR^9$ may of course, be further treated with standard oxidizing reagents such as potassium permanganate, metachloroperbenzoic acid, or the like using conditions analogous to those known for similar reactions to obtain a compound of Formula $I^4$ wherein $R^9$ is as defined above. The preparation of compounds of Formula I wherein $R^3$ is a sulfur containing group as described hereinabove is shown in Scheme VIII.

Particularly, the processes described above include compounds wherein $R^1$ is 5-methoxy, Q is hydrogen, and $R^2$ is phenyl or benzyl beginning with either a commercially available compound or a compound described by Y. Murakami, et al. in *Synthesis* p 738 (1984).

The 3-alkoxy carboxylic acids of Formula III may be purified by conventional methods or employed without separation in the step shown in Scheme I.

This step is accomplished by methods known in the art, for example, by coupling the 3-alkoxy carboxylic acids of Formula III with 5-aminotetrazole of Formula II, in the presence of coupling agents. Such agents include 1,1'-carbonyldiimidazole, dicyclohexylcarbodiimide, and the like. See Scheme II. Appropriate solvents for the step shown in Scheme II may be, for example, N,N-dimethylforamide (DMF), acetonitrile, tetrahydrofuran, chloroform, or dichloromethane. Recrystallization of compounds I, may be accomplished in various solvents, such as N,N-dimethylformamide (DMF) either alone or in combination with $H_2O$, acetonitrile in combination with water or with DMF and water, acetone, ethyl acetate, methanol alone or in combination with water, 2-methoxyethanol in combination with water, 2-propanol either in combination with water or in combination with water or in combination with DMF and water.

The starting materials required for the processes described in this invention are either commercially available or they can be synthesized by methods known in the art of organic chemistry. For example, an acid intermediate having the Formula III wherein $R^1$, Q, and $R^2$ are hydrogen, $R^3$ is methoxy, is described by N. T. Modi, et al, *J. Org. Chem.*, Vol. 35, 2228 (1970), and a methyl ester of the compound having the Formula III, wherein $R^1$ and Q are hydrogen, $R^2$ is methyl, is as described in French Pat. No. 1,503,908 (see Chem. Abst., Vol. 70, 37, 651 (1969). Likewise, an ester of the acid having the Formula III, wherein $R^1$ is methoxy or chloro, Q is hydrogen, $R^2$ is phenyl or 4-methoxyphenyl, $R^3$ is hydroxy, can be prepared in a manner analogous to that described by P. Friedlander, et al, *Chem. Ber.*, Vol. 55, 1597 (1922). Also, various esters of acids of indole compounds for use as precursors in a process of the present invention can be made in view of the teachings of P. C. Unangst, et al, *J. Heterocyclic Chem.*, Vol. 21, 709 (1984).

Under certain circumstances it is necessary to protect either the N or O of intermediates in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (New York, 1973), pages 43ff, 95ff; (2) J. F. W. McOmie, *Advances in Organic Chemistry*, Vol. 3, 191–281 (1963); (3) R. A. Borssonas, *Advances in Or-*

*ganic Chemistry*, Vol. 3, 159–190 (1963); and (4) J. F. W. McOmie, *Chem. & Ind.*, 603 (1979).

Examples of suitable oxygen protecting groups are benzyl, t-butyldimethylsilyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of Formula I described above are prepared by reacting the appropriate base with a stoichometric equivalent of the acid indole compounds of Formula I to obtain pharmacologically acceptable salts thereof.

The compounds of this invention may also exist in hydrated or solvated forms.

DESCRIPTION OF THE PREFERRED EMBODIMENTS

The process of this invention is further elaborated by the representative examples as follows.

EXAMPLE 1

3-Methoxy-1-(phenylmethyl)-1H-indole-2-carboxylic acid

A mixture of 4.6 g (0.096 mole) of 50% sodium hydride/mineral oil in 100 ml of N,N-dimethylformamide under a nitrogen atmosphere was cooled in an ice bath. To the stirred mixture was added over 45 minutes, a solution of 19.5 g (0.089 mole) of 3-methoxy-1H-indole-2-carboxylic acid ethyl ester [A. Galun, A. Markus, and A. Kampf, *J. Heterocyclic Chem.*, 16, 221 (1979)] in 50 ml of N,N-dimethylformamide. The mixture was stirred for an additional 30 minutes, and a solution of 11.6 ml (16.7 g; 0.098 mole) of benzyl bromide in 10 ml of N,N-dimethylformamide was added over 15 minutes. The ice bath was removed, the mixture was stirred for an additional 16 hours, and then added to 800 g of ice water. The crude ester intermediate was removed by extracting with dichloromethane (4×250 ml). The combined organic layers were back-washed with brine (3×500 ml), dried (anhydrous sodium sulfate), and evaporated to yield a crude residue of 3-methoxy-1(phenylmethyl)-1H-indole-2-carboxylic acid ethyl ester, plus a small amount of N,N-dimethylformamide.

The total crude residue described above was dissolved in 180 ml of methanol and treated with a solution of 14.2 g (0.25 mole) of potassium hydroxide in 180 ml of water. The mixture was stirred at reflux for three hours, cooled, condensed to approximately one-third its original volume (rotary evaporator), and partitioned between 750 ml of water and 300 ml of dichloromethane. The aqueous layer was separated, washed with fresh dichloromethane (2×300 ml), filtered, and cooled in ice. Acidification with 4.0N hydrochloric acid yielded the crude carboxylic acid product. The product was filtered and washed with water to yield 17.1 g (68% yield) of final product. A sample recrystallized from ethyl acetate/hexane was analytically pure, mp 115°–117° C.

EXAMPLE 2

1-Hexyl-3-methoxy-1H-indole-2-carboxylic acid

Prepared by the procedure described in Example 1 from 27.0 g (0.12 mole) of 3-methoxy-1H-indole-2-carboxylic acid ethyl ester [A. Galun, A. Markus, and A. Kampf, *J. Heterocyclic Chem.*, 16, 221 (1979)] alkylated with 22.1 g (0.13 mole) of 1-bromohexane.

Saponification of 20.7 g (0.068 mole) of the crude intermediate 1-hexyl-3-methoxy-1H-indole-2-carboxylic acid ethyl ester as described in Example 1 yielded 14.1 g (75% yield) of the crude carboxylic acid product. A sample recrystallized several times from hexane was analytically pure, mp 65°–67° C.

EXAMPLE 3

3,5-Dimethoxy-1-phenyl-1H-indole-2-carboxylic acid

A mixture of 10.8 g (0.036 mole) of 3-hydroxy-5-methoxy-1-phenyl-1H-indole-2-carboxylic acid methyl ester [P. C. Unangst and M. E. Carethers, *J. Heterocyclic Chem.*, 21, 709 (1984)] and 5.5 g (0.040 mole) of anhydrous potassium carbonate in 100 ml of acetone was treated with 3.7 ml (4.9 g; 0.039 mole) of dimethyl sulfate. The mixture was stirred and heated at reflux for 16 hours, cooled, and filtered. The filter cake was washed several times with fresh acetone, and the combined filtrates were evaporated (vacuum) to yield a crude residue of 3,5-dimethoxy-1-phenyl-1H-indole-2-carboxylic acid methyl ester.

The total crude residue described above was saponified with 6.3 g (0.11 mole) of potassium hydroxide by the procedure described in Example 1. There was obtained 9.8 g (91% yield) of crude carboxylic acid. Recrystallization from aqueous acetone yielded the carboxylic acid product in analytical purity, mp 150° C.-dec.

EXAMPLE 4

3-Methoxy-1-phenyl-1H-indole-2-carboxylic acid

A suspension of 3.9 g (0.081 mole) of 50% sodium hydride/mineral oil in 85 ml of N,N-dimethylformamide under a nitrogen atmosphere was cooled in ice and treated portionwise over 90 minutes with 17.1 g (0.064 mole) of 3-hydroxy-1-phenyl-1H-indole-2-carboxylic acid methyl ester [P. Friedlander and K. Kunz, *Chem. Ber.*, 55, 1597 (1922)]. The mixture was stirred in ice an additional one hour, 7.9 ml (10.5 g; 0.083 mole) of dimethyl sulfate was added dropwise over 15 minutes, the ice bath was removed, and stirring was continued for a total of 65 hours. The reaction mixture was added to 600 g of ice/water, acidified with 4.0N hydrochloric acid, and extracted with dichloromethane (4×250 ml). The combined organic layers were washed with water (3×500 ml), dried (anhydrous sodium sulfate), and evaporated to yield a crude residue of 3-methoxy-1-phenyl-1H-indole-2-carboxylic acid methyl ester, plus a small amount of N,N-dimethylformamide.

The total crude residue described above was saponified with 11.4 g (0.20 mole) of potassium hydroxide by the procedure described in Example 1. There was obtained 14.4 g (84% yield) of crude carboxylic acid product. A sample recrystallized from ethyl acetate/hexane was analytically pure, mp 115° C.-dec.

EXAMPLE 5

1-Phenyl-3-(phenylmethoxy)-1H-indole-2-carboxylic acid methyl ester

A mixture of 1.2 g (0.025 mole) of 50% sodium hydride/mineral oil suspension in 20 ml of hexamethylphosphoramide under a nitrogen atmosphere was cooled in ice and treated over 15 minutes with a solution of 5.3 g (0.020 mole) of 3-hydroxy-1-phenyl-1H-indole-2-carboxlic acid methyl ester [P. Friedlander and K. Kurz, *Chem. Ber.*, 55, 1597 (1922)] in 25 ml of hexamethylphosphoramide. The mixture was stirred in ice an additional one hour, 2.6 ml (2.9 g, 0.023 mole) of benzyl chloride was added in one portion, the ice bath was removed and stirring was continued for a total of 18 hours. The reaction mixture was added to 200 g of ice/water, stirred for one hour, and the precipitated product was filtered and washed with water. Recrystallization from aqueous methanol yielded 3.8 g (54% yield) of the ester product. An additional recrystallization as above yielded analytically pure ester, mp 117°–119° C.

EXAMPLE 6

1-Phenyl-3-(phenylmethoxy)-1H-indole-2-carboxylic acid

A mixture of 11.9 g (0.033 mole) of the ester described in Example 5 in 200 ml of dimethyl sulfoxide under a nitrogen atmosphere was treated with 7.4 g (0.066 mole) of potassium tert-butoxide. The mixture was stirred and heated to 65° C. for two hours, cooled, and added to 2.5 kg ice/water. The aqueous mixture was filtered, and the filtrate was cooled in ice and acidified with 6.0N hydrochloric acid to precipitate the crude carboxylic acid product. The product was filtered and washed with water to yield 9.7 g (89% yield) of final product. A sample recrystallized from ethyl acetate/hexane was analytically pure, mp 140°–142° C.

EXAMPLE 7

5-Methoxy-1-phenyl-3-(phenylmethoxy)-1H-indole-2-carboxylic acid

A mixture of 155 g (0.52 mole) of 3-hydroxy-5-methoxy-1-phenyl-1H-indole-2-carboxylic acid methyl ester [P. C. Unangst and M. E. Carethers, *J. Heterocyclic Chem.*, 21, 709 (1984)], 83.0 g (0.60 mole) of anhydrous potassium carbonate, and 68 ml (97.8 g; 0.57 mole) of benzyl bromide in 2250 ml of acetone was stirred at reflux for 20 hours. The mixture was cooled, filtered, and the filter cake was washed several times with fresh acetone. The combined filtrates were evaporated (vacuum) to yield a crude residue of 5-methoxy-1-phenyl-3-(phenylmethoxy)-1H-indole-2-carboxylic acid methyl ester.

The total crude residue described above was dissolved in 1.0 l of methanol. The solution was treated with a solution of 83 g (1.48 mole) of potassium hydroxide in 1.0 l of water, and the new mixture was stirred at reflux for three hours. The reaction mixture was cooled, filtered, and the filtrate was added to 7.0 kg of ice/water. The aqueous solution was cooled in ice and acidified with glacial acetic acid to precipitate the crude carboxylic acid product. The product was filtered and washed with water to yield 174 g (89% yield) of final product. A sample recrystallized from aqueous acetone was analytically pure, mp 123° C.-dec.

EXAMPLE 8

5-Methoxy-3-(1-methylethoxy)-1-phenyl-1H-indole-2-carboxylic acid

A stirred mixture of 24.8 g (0.22 mole) of potassium tert-butoxide in 100 ml of dimethyl sulfoxide (under a nitrogen atmosphere) was placed in a cold water bath. A solution of 44.6 g (0.15 mole) of 3-hydroxy-5-methoxy-1-phenyl-1H-indole-2-carboxylic acid methyl ester [P. C. Unangst and M. E. Carethers, *J. Heterocyclic Chem.*, 21, 709 (1984)] in 100 ml of dimethyl sulfoxide was added over 30 minutes. The new mixture was stirred for an additional 45 minutes, and 25.0 ml (32.8 g, 0.27 mole) of 2-bromopropane was added in one portion. The cooling bath was removed, and the mixture was stirred at room temperature for 45 hours, then added to 2.5 kg ice water. The crude ester intermediate was removed by extracting with dichloromethane (4×800 ml). The combined organic layers were washed with water (1×2.0 l), 5% aqueous sodium bicarbonate (2×2.0 l), and water again (1×2.0 l), before being dried with anhydrous sodium sulfate. Evaporation (vacuum) yielded a crude residue of 5-methoxy-3-(1-methylethoxy)-1-phenyl-1H-indole-2-carboxylic acid methyl ester.

The total crude residue described above was dissolved in 300 ml of methanol and the solution was treated with a solution of 22.5 g (0.40 mole) of potassium hydroxide in 300 ml of water. The mixture was stirred at reflux for three hours, cooled, and condensed on a rotary evaporator until a precipitate began to form. After standing for several hours, the precipitated carboxylic acid potassium salt was filtered and washed with cold acetone. The solid was dissolved in 850 ml of water plus 140 ml of acetone by warming slightly. The new solution was cooled in ice and treated with 10 ml of glacial acetic acid to precipitate the crude product. The solid was filtered and washed with water to yield 33.4 g (68% yield) of the carboxylic acid product. A sample recrystallized from aqueous methanol was analytically pure, mp 110° C.-dec.

EXAMPLE 9

3-Ethoxy-5-methoxy-1-phenyl-1H-indole-2-carboxylic acid

Prepared by the procedure described in Example 8 from 30.0 g (0.10 mole) of 3-hydroxy-5-methoxy-1-phenyl-1H-indole-2-carboxylic acid methyl ester alkylated with 67.5 ml (79.4 g; 0.51 mole) of diethyl sulfate.

The crude 3-ethoxy-5-methoxy-1-phenyl-1H-indole-2-carboxylic acid methyl ester intermediate was saponified as described in Example 1 to yield 27.5 g (88% yield) of the crude carboxylic acid product. A sample recrystallized several times from aqueous methanol was analytically pure, mp 130° C.-dec.

EXAMPLE 10

3-Hydroxy-1-(4-methoxyphenyl)-1H-indole-2-carboxylic acid methyl ester

Prepared in a manner analogous to the multi-step procedure described [P. Friedlander and K. Kunz, *Chem. Ber.*, 55, 1597 (1922)] for the preparation of 3-hydroxy-1-phenyl-1H-indole-2-carboxylic acid methyl ester, with 2-(4-methoxyphenylamino)benzoic acid substituted for 2-(phenylamino)benzoic acid in the first step of the synthetic sequence. The final indole product was recrystallized from 2-propanol to yield analytically pure product, mp 153°–155° C.

EXAMPLE 11

1-(4-Methoxyphenyl)-3-(1-methylethoxy)-1H-indole-2-carboxylic acid methyl ester

Prepared by the procedure described in Example 8 from 5.0 g (0.017 mole) of 3-hydroxy-1-(4-methoxyphenyl)-1H-indole-2-carboxylic acid methyl ester alkylated with 3.6 ml (4.7 g; 0.038 mole) of 2-bromopropane. After addition of the total reaction mixture to water, the precipitate was filtered and washed with water to yield 5.6 g (95% yield) of crude ester product. A sample recrystallized from methanol was analytically pure, mp 129°–131° C.

EXAMPLE 12

1-(4-Methoxyphenyl)-3-(1-methylethoxy)-1H-indole-2-carboxylic acid

Prepared by the saponification procedure described in Example 7 from 5.0 (0.015 mole) of 1-(4-methoxyphenyl)-3-(1-methylethoxy)-1H-indole-2-carboxylic acid methyl ester and 12.0 g (0.20 mole) of potassium hydroxide. The crude product was recrystallized from ether/hexane to yield 3.8 g (78% yield) of analytically pure carboxylic acid product, mp 129° C.-dec.

EXAMPLE 13

5-Chloro-3-hydroxy-1-phenyl-1H-indole-2-carboxylic acid methyl ester

Prepared in a manner analogous to the multistep procedure described [P. Friedlander and K. Kunz, Chem. Ber., 55, 1597 (1922)] for the preparation of 3-hydroxy-1-phenyl-1H-indole-2-carboxylic acid methyl ester, with 5-chloro-2-(phenylamino)benzoic acid substituted for 2-(phenylamino)benzoic acid in the first step of the synthetic sequence. The final indole product was recrystallized from aqueous 2-methoxyethanol to yield analytically pure product, mp 170°–173° C.

EXAMPLE 14

5-Chloro-3-(1-methylethoxy)-1-phenyl-1H-indole-2-carboxylic acid

Prepared by the procedure described in Example 8 from 13.9 g (0.046 mole) of 5-chloro-3-hydroxy-1-phenyl-1H-indole-2-carboxylic acid methyl ester alkylated with 7.7 ml (10.1 g; 0.082 mole) of 2-bromopropane.

The crude 5-chloro-3-(1-methylethoxy)-1-phenyl-1H-indole-2-carboxylic acid methyl ester intermediate (14.8 g; 0.043 mole) was saponified with 6.4 g (0.11 mole) of potassium hydroxide as described in Example 1 to yield 10.2 g (72% yield) of the crude carboxylic acid product, mp 120° -dec. This material was used for further synthesis without additional purification.

EXAMPLE 15

3-Methoxy-1-nonyl-1H-indole-2-carboxylic acid

Prepared by the procedure described in Example 1 from 20.0 g (0.091 mole) of 3-methoxy-1H-indole-2-carboxylic acid ethyl ester [A. Galun, A. Markus, and A. Kampf, J. Heterocyclic Chem., 16, 221 (1979)], alkylated with 19 ml (20.6 g; 0.099 mole) of n-nonyl bromide.

The crude 3-methoxy-1-nonyl-1H-indole-2-carboxylic acid ethyl ester intermediate was saponified as described in Example 1 to yield 18.0 g (62% yield) of the crude carboxylic acid product. This material was used for further synthesis without additional purification.

EXAMPLE 16

3-(1-Methylethoxy)-1-phenyl-1H-indole-2-carboxylic acid

Prepared by the procedure described in Example 8 from 9.5 g (0.036 mole) of 3-hydroxy-1-phenyl-1H-indole-2-carboxylic acid methyl ester [P. Friedlander and K. Kunz; Chem. Ber., 55, 1597 (1922)], alkylated with 5.9 ml (7.7 g; 0.063 mole) of 2-bromopropane.

The crude 3-(1-methylethoxy)-1-phenyl-1H-indole-2-carboxylic acid methyl ester intermediate was saponified as described in Example 1 to yield 8.3 g (79% yield) of the crude carboxylic acid product, mp 100°-dec. This material was used for further synthesis without additional purification.

EXAMPLE 17

5-Methoxy-3-(n-nonyloxy)-1-phenyl-1H-indole-2-carboxylic acid

Prepared by the procedure described in Example 7 from 20.0 g (0.067 mole) of 3-hydroxy-5-methoxy-1-phenyl-1H-indole-2-carboxylic acid methyl ester [P. C. Unangst and M. E. Carethers, J. Heterocyclic Chem., 21, 709 (1984)], alkylated with 14 ml (15.2 g; 0.073 mole) of n-nonyl bromide.

A 1.0 g (0.0024 mole) sample of the crude 5-methoxy-3-(n-nonyloxy)-1-phenyl-1H-indole-2-carboxylic acid methyl ester intermediate was saponified as described in Example 6 (except that the saponification was carried out at 25° C. for 18 hours) to yield 0.35 g (36% yield) of the crude carboxylic acid product, mp 81°–84° C. This material was used for further synthesis without additional purification.

EXAMPLE 18

3-(n-Dodecyloxy)-5-methoxy-1-phenyl-1H-indole-2-carboxylic acid

Prepared by the procedure described in Example 8 from 10.0 g (0.034 mole) of 3-hydroxy-5-methoxy-1-phenyl-1H-indole-2-carboxylic acid methyl ester [P. C. Unangst and M. E. Carethers, J. Heterocyclic Chem., 21, 709 (1984)], alkylated with 12.6 g (0.037 mole) of n-dodecyl p-toluene-sulfonate [C. S. Marvel and V. C. Sekera, Organic Syntheses Coll. Vol. 3, p. 366].

A 1.0 g (0.0022 mole) sample of the crude 3-(n-dodecyloxy)-5-methoxy-1-phenyl-1H-indole-2-carboxylic acid methyl ester intermediate was saponified as described in Example 6 (except that the reaction was carried out at 25° C. for 21 hours) to yield 0.38 g (39% yield) of the crude carboxylic acid product, mp 85°–87° C. This material was used for further synthesis without additional purification.

EXAMPLE 19

2-[(Carboxymethyl)methylamino]-5-methoxybenzoic acid

A mixture of 244 g (0.91 mole) of the potassium salt of 2-bromo-5-methoxybenzoic acid (prepared by treating a solution of the parent carboxylic acid in 2-propanol with excess methanolic potassium hydroxide), 196 g (1.54 mole) of the potassium salt of N-methylglycine (prepared as above), 13 g (0.82 mole) of anhydrous potassium carbonate and 0.66 g (0.01 mole) of copper powder in 220 ml of water was stirred at reflux for five hours. The mixture was cooled, added to 4.0 kg of ice/-

3-(n-Dodecyloxy)5-methoxy-1-phenyl-N-1H-tetrazol-5-yl-1H-indole-2-carboxamide, mp 185°-186° C.

EXAMPLE 26

5-Methoxy-3-(1-methylethoxy)-1-phenyl-N-1H-tetrazol-5-yl-1H-indole-2-carboxamide L-arginate salt A suspension of 2.76 g (0.007 mole) of 5-methoxy-3-(1-methylethoxy)-1-phenyl-N-1H-tetrazol-5-yl-1H-indole-2-carboxamide in 40 ml of methanol was warmed on a steam bath and treated with a solution of 1.22 g (0.007 mole) of L-arginine dissolved in a minimum of hot water. The mixture was digested until nearly one phase and filtered hot. Cooling to room temperature resulted in precipitation of the arginine salt product. The solid was filtered and washed several times with cold acetone to yield 2.77 g (70% yield) of analytically pure arginine salt, containing 0.50 mole of water of hydration, mp 218° C.-dec.

EXAMPLE 27

5-Methoxy-3-(1-methylethoxy)-1-phenyl-N-1-tetrazol-5-yl-1H-indole-2-carboxamide sodium salt A suspension of 7.85 g (0.020 mole) of 5-methoxy-3-(1-methylethoxy)-1-phenyl-N-1H-tetrazol-5-yl-1H-indole-2-carboxamide in 175 ml of methanol was warmed on the steam bath and treated with 10.0 ml of 2.0N aqueous sodium hydroxide solution. The mixture was digested for a few minutes, filtered hot, cooled, and evaporated. The residue was dissolved and reevaporated several times in 50% acetone/methanol. There was obtained 7.5 g (90% yield) of the amorphous sodium salt product, analytically pure containing 1.0 equivalent of water of hydration, mp 205° C.-dec.

EXAMPLE 28

3-Ethoxy-5-methoxy-1-phenyl-N-1H-tetrazol-5-yl-1H-indole-2-carboxamide L-arginate salt Prepared by the procedure described in Example 26 from 2.8 g (0.0074 mole) of 3-ethoxy-5-methoxy-1-phenyl-N-1H-tetrazol-5-yl-1H-indole-2-carboxamide and 1.3 g (0.0075 mole) of L-arginine, except that the solvent was ethanol rather than methanol. There was obtained 2.6 g (63% yield) of the arginine salt product, analytically pure containing 1.0 equivalent of water of hydration, mp 165° C.-dec.

EXAMPLE 29

3-Ethoxy-5-methoxy-1-phenyl-N-1H-tetrazol-5-yl-1H-indole-2-carboxamide sodium salt Prepared by the procedure described in Example 27 from 7.57 g (0.020 mole) of 3-ethoxy-5-methoxy-1-phenyl-N-1H-tetrazol-5-yl-1H-indole-2-carboxamide, and 10.0 ml of 2.0N aqueous sodium hydroxide solution. There was obtained 7.27 g (91% yield) of the amorphous sodium salt product, analytically pure containing 0.50 equivalent of water of hydration, mp 195° C.-dec.

EXAMPLE 30

2-[(Cyanomethyl)phenylamino]-5-methoxybenzoic acid methyl ester

A mixture of 7.1 g (0.025 mole) of 2-[(cyanomethyl)phenylamino]-5-methoxybenzoic acid [P. C. Unangst and M. E. Carethers, *J. Heterocyclic Chem.*, 21, 709 (1974)], 4.0 g (0.029 mole) of anhydrous potassium carbonate, and 3.0 ml (4.0 g; 0.032 mole) of dimethyl sulfate in 200 ml of acetonitrile was stirred at reflux for 24 hours. The mixture was cooled and filtered, and the filter cake was washed several times with fresh acetonitrile. The combined filtrates were evaporated to an oil, which crystallized upon standing at room temperature. Recrystallization from aqueous methanol yielded 5.1 g (68% yield) of the ester product. A sample recrystalized again as above was analytically pure, mp 107°-109° C.

EXAMPLE 31

3-Hydroxy-5-methoxy-1-phenyl-1H-indole-2-carbonitrile

A mixture of 8.4 g (0.075 mole) of potassium tert.-butoxide in 200 ml of tetrahydrofuran (under a nitrogen atmosphere) was stirred and cooled in an ice bath. A solution of 13.7 g (0.046 mole) of 2-[(cyanomethyl)phenylamino]-5-methoxybenzoic acid methyl ester in 150 ml of tetrahydrofuran was added over two hours, the ice bath was removed, and the new mixture was stirred for an additional 42 hours. The total reaction mixture was added to 1.1 kg of ice/water and acidified with 12.0 ml of glacial acetic acid to precipitate the crude product. The solid was filtered, washed with water, and recrystallized from aqueous methanol to yield 10.3 g (84% yield) of the nitrile product. A sample recrystallized again as above was analytically pure, mp 182° C.-dec.

EXAMPLE 32

3-Ethoxy-5-methoxy-1-phenyl-1H-indole-2-carbonitrile

Prepared by the procedure described in Example 8 from 2.2 g (0.0083 mole) of 3-hydroxy-5-methoxy-1-phenyl-1H-indole-2-carbonitrile alkylated with 3.3 ml (3.9 g; 0.025 mole) of diethyl sulfate. The crude product was recrystallized from aqueous propanol to yield 1.6 g (67% yield) of the alkylated nitrile product. An additional recrystallization as above yielded an analytically pure sample, mp 97°-99° C.

EXAMPLE 33

3-(Diethylamino)-5-methoxy-1H-indole-2-carboxylic acid, ethyl ester

A stirred solution of 12.0 g (0.051 mole) of 3-amino-5-methoxy-1H-indole-2-carboxylic acid, ethyl ester (S. V. Simakov, et al, *Khim-Farm Zh.*, 17, 1183 (1983) and 11.5 g (0.26 mole) of acetaldehyde in 250 ml of acetonitrile (under a nitrogen atmosphere) was cautiously treated with 14.0 g (0.22 mole) of sodium cyanoborohydride. After stirring for 15 minutes, 4.0 ml (4.2 g; 0.07 mole) of acetic acid was added in portions over two hours. The reaction mixture was poured over a mixture of ice and 400 ml of 1.0N sodium hydroxide solution, and the new mixture was extracted with ether. The combined ether layers were washed several times with brine, dried (anhydrous magnesium sulfate), and evaporated to an orange oil. Flash chromatographic purification (silica gel, methylene chloride/ethyl acetate/hexane (1:6:3) elution) of the residual oil yielded 11.5 g (76% yield) of the analytically pure ester product, mp 85°-89° C.

EXAMPLE 34

3-(Diethylamino-5-methoxy-1-phenyl-N-1H-tetrazol-5-yl-1H-indole-2-carboxamide

A mixture of 3.0 g (0.010 mole) of 3-(diethylamino)-5-methoxy-1H-indole-2-carboxylic acid, ethyl ester, 5.0 g (0.036 mole) of potassium carbonate, 0.50 g (0.009 mole) of potassium hydroxide, 0.30 g (0.001 mole) of copper-(I)bromide, and 30.0 ml (44.7 g; 0.28 mole) of bromobenzene under an argon atmosphere was stirred and heated at reflux for three hours. The reaction mixture water, and acidified with concentrated hydrochloric acid to precipitate the crude product. The solid was filtered and washed with water to yield 186 g (86% yield) of the carboxylic acid product. A sample recrystallized from aqueous 2-methoxyethanol was analytically pure, mp 196° C.-dec.

EXAMPLE 20

2-[(Carboxymethyl)methylamino]-5-methoxybenzoic acid dimethyl ester

A mixture of 186 g (0.78 mole) of 2-[(carboxymethyl)methylamino]-5-methoxybenzoic acid in 1.0 l of N,N-dimethylformamide was stirred and treated with a 25% aqueous solution of sodium hydroxide (62.2 g; 1.56 mole). The mixture was stirred for an additional 20 minutes, and 139 ml (316 g; 2.22 mole) of iodomethane was added in one portion. After stirring for 16 hours, the mixture was added to 4.0 kg of ice/water, and the ester product was removed by extracting with dichloromethane (4×1.5 l). The combined organic layers were washed with water (1×2.0 l), saturated aqueous sodium bicarbonate (3×2.0 l), and water again, dried (anhydrous sodium sulfate), and evaporated. The crude diester residue (containing some residual N,N-dimethylformamide) was cyclized to the corresponding indole without additional purification.

EXAMPLE 21

3-Hydroxy-5-methoxy-1-methyl-1H-indole-2-carboxylic acid methyl ester

The total crude diester residue described in Example 20 was dissolved in 1.0 l of methanol under a nitrogen atmosphere. To the stirred mixture was added 54.6 g (1.01 mole) of sodium methoxide in one portion. The mixture was stirred at reflux for three hours, cooled, added to 4.0 kg of ice/water, and acidified with glacial acetic acid to precipitate the product. The solid was filtered and washed with water to yield 71.7 g (39% yield) of the indole product. A sample recrystallized from aqueous methanol was analytically pure, containing 0.25 mole of water of hydration, mp 103°-105° C.

EXAMPLE 22

5-Methoxy-1-methyl-3-(1-methylethoxy)-1H-indole-2-carboxylic acid methyl ester

Prepared by the procedure described in Example 8 from 69.6 g (0.30 mole) of 3-hydroxy-5-methoxy-1-methyl-1H-indole-2-carboxylic acid methyl ester alkylated with 27.8 ml (36.3 g; 0.30 mole) of 2-bromopropane. After addition of the total reaction mixture to water, the precipitate was filtered and washed with water to yield 45 g (55% yield) of crude ester product. A sample recrystallized from aqueous methanol was analytically pure, mp 87°-89° C.

EXAMPLE 23

5-Methoxy--methyl-3-(1-methylethoxy)-1H-indole-2-carboxylic acid

Prepared by the saponification procedure described in Example 7 from 41.2 g (0.15 mole) of 5-methoxy-1-methyl-3-(1-methylethoxy)-1H-indole-2-carboxylic acid methyl ester and 16.7 g (0.30 mole) of potassium hydroxide. The crude acid product was 18.3 g (47% yield). A sample recrystallized from aqueous 2-methoxyethanol was analytically pure, mp 110°-112° C.

EXAMPLE 24 (PROCEDURE A)

3-Methoxy-1-(phenylmethyl)-N-1H-tetrazol-5-yl-1H-indole-2-carboxamide

A mixture of 3.0 g (0.011 mole) of 3-methoxy-1-(phenylmethyl)-1H-indole-2-carboxylic acid and 3.7 g (0.023 mole) of 1,1'-carbonyldiimidazole in 15 of N,N-dimethylformamide was stirred and heated on the steam bath under a nitrogen atmosphere for 20 minutes. The mixture was cooled, 1.3 g (0.013 mole) of 5-aminotetrazole monohydrate was added, and heating was continued for an additional 20 minutes. The cooled reaction mixture was added to 150 g of ice/water. Acidification with 4.0N hydrochloric acid yielded the carbamoyltetrazole product. The crude product was filtered, washed with water, and recrystallized from 2-methoxyethanol/water to yield analytically pure product. There was obtained 2.3 g (63% yield) of product, mp 230° C.-dec.

EXAMPLE 25 (PROCEDURE B)

5-Methoxy-3-(1-methylethoxy)-1-phenyl-N-1H-tetrazol-5-yl-1H-indole-2-carboxamide A mixture of 20.0 g (0.062 mole) of 5-methoxy-3-(1-methylethoxy)-1-phenyl-1H-indole-2-carboxylic acid and 11.3 g (0.070 mole) of 1,1'-carbonyldiimidazole in 375 ml of acetonitrile was stirred at reflux (under a nitrogen atmosphere) for 90 minutes. The mixture was cooled, and 6.2 g (0.073 mole) of anhydrous 5-aminotetrazole was added, followed by 20.6 ml (15 g; 0.15 mole) of triethylamine. After stirring at reflux for an additional 16 hours, the mixture was cooled, added to 1.5 kg of ice/water and acidified with glacial acetic acid. The precipitated product was filtered and washed with water. Recrystallization from aqueous acetonitrile yielded 19.0 g (79% yield) of analytically pure carbamoyltetrazole product, mp 227° C.-dec.

Additionally the following compounds of Formula I may be prepared by methods analogous to Procedures A or B above:

3-Methoxy-N-1H-tetrazol-5-yl-1H-indole-2-carboxamide, mp 235° C.-dec.

3-Methoxy-1-methyl-N-1H-tetrazol-5-yl-1H-indole-2-carboxamide, mp 240° C.-dec.

1-Hexyl-3-methoxy-N-1H-tetrazol-5-yl-1H-indole-2-carboxamide, mp 210° C.-dec.

3-Methoxy-1-nonyl-N-1H-tetrazol-5-yl-1H-indole-2-carboxamide, mp 199°-200° C.

3-Methoxy-1-phenyl-N-1H-tetrazol-5-yl-1H-indole-2-carboxamide, mp 215° C.-dec.

1-Phenyl-3-(phenylmethoxy)-N-1H-tetrazol-5-yl-1H-indole-2-carboxamide, mp 208° C.-dec.

3-(1-Methylethoxy)-1-phenyl-N-1H-tetrazol-5-yl-1H-indole-2-carboxamide, mp 203°-205° C.

1-(4-Methoxyphenyl)-3-(1-methylethoxy)-N-1H-tetrazol-5-yl-1H-indole-2-carboxamide, mp 166° C.-dec.

5-Chloro-3-(1-methylethoxy)-1-phenyl-N-1H-tetrazol-5-yl-1H-indole-2-carboxamide, mp 228° C.-dec.

5-Methoxy-1-methyl-3-(1-methylethoxy)-N-1H-tetrazol-5-yl-1H-indole-2-carboxyamide, mp 222°-225° C.

3,5-Dimethoxy-1-phenyl-N-1H-tetrazol-5-yl-1H-indole-2-carboxamide, mp 220° C.-dec.

3-Ethoxy-5-methoxy-1-phenyl-N-1H-tetrazol-5-yl-1H-indole-2-carboxamide, mp 226° C.-dec.

5-Methoxy-1-phenyl-3-(phenylmethoxy)-N-1H-tetrazol-5-yl-1H-indole-2-carboxamide, mp 212° C.-dec.

5-Methoxy-3-(n-nonyloxy)-1-phenyl-N-1H-tetrazol-5-yl-1H-indole-2-carboxamide, mp 203°-204° C.

was filtered while hot through a bed of Celite filter-aid. The filter cake was washed twice with warm toluene, and the combined filtrates were evaporated. The residue was dissolved in a small amount of dichloromethane and purified by flash chromatography (silica gel, 15% ethyl acetate in hexane elution) to yield 2.4 g (66% yield) of intermediate, 3-(diethylamino)-5-methoxy-1-phenyl-1H-indole-2-carboxylic acid, ethyl ester, as an oil.

A solution of 2.0 ml (1.44 g; 0.014 mole) of diisopropylamine in 20 ml of tetrahydrofuran under a nitrogen atmosphere was cooled to −10° C. and treated with 5.4 ml (0.014 mole) of 2.6M n-butyllithium in hexane. After stirring for five minutes, a solution of 0.43 g (0.0051 mole) of anhydrous 5-aminotetrazole in 20 ml of 1,3-dimethyl-2-imidazolidinone was added dropwise. The reaction mixture was stirred for two hours at −10° C., and then a solution of 1.7 g (0.0046 mole) of the previously described 3-(diethylamino)-5-methoxy-1-phenyl-1H-indole-2-carboxylic acid, ethyl ester in 20 ml of tetrahydrofuran was added dropwise. The new mixture was stirred for three hours at −10° C., then quenched by the addition of aqueous saturated ammonium chloride solution. The total reaction mixture was added to 100 ml of ice water and extracted twice with ether (organic layers discarded). The aqueous phase was cooled in ice and acidified to pH 4 with dilute hydrochloric acid to precipitate 0.25 g (13% yield) of the carbamoyltetrazole product, mp 105°–112° C.

EXAMPLE 35

5-Methoxy-1-phenyl-1H-indole-2-carboxylic acid

A mixture of 60.0 g (0.32 mole) of 5-methoxy-1H-indole-2-carboxylic acid, 35.0 ml (52.2 g; 0.32 mole) of bromobenzene, 36.0 g (0.64 mole) of potassium hydroxide, and 10.0 g (0.13 mole) of copper (II) oxide in 750 ml of N,N-dimethylformamide was stirred and heated at reflux under a nitrogen atmosphere for six hours. The cooled reaction mixture was added to 1.5 kg of ice/water and filtered through a bed of Celite filter-aid. Acidification of the filtrate with dilute hydrochloric acid precipitated the product. The solid was filtered and washed with water to yield 83.0 g (95% yield) of crude acid product. A sample recrystallized from ether/hexane was analytically pure, mp 197°–204° C.

EXAMPLE 36

5-Methoxy-1-phenyl-1H-indole-2-carboxylic acid, methyl ester

A solution of 30.0 g (0.11 mole) of 5-methoxy-1-phenyl-1H-indole-2-carboxylic acid in 300 ml of N,N-dimethylformamide was treated with 9.6 g (0.12 mole) of 50% aqueous sodium hydroxide solution. The new mixture was stirred for 15 minutes, 8.0 ml (18.4 g; 0.13 mole) of iodomethane was added, and stirring was continued at room temperature for four hours. The reaction mixture was added to 1.0 l of cold water and extracted with dichloromethane. The combined organic layers were washed twice with water, dried (anhydrous magnesium sulfate) and evaporated. Recrystallization of the residue from petroleum ether yielded 25 g (82% yield) of the analytically pure ester product, mp 67°–68° C.

EXAMPLE 37

5-Methoxy-3-(methylsulfinyl)-1-phenyl-1H-indole-2-carboxylic acid, methyl ester

A mixture of 4.0 g (0.014 mole) of 5-methoxy-1-phenyl-1H-indole-2-carboxylic acid, methyl ester in 7.0 ml (11.4 g; 0.096 mole) of thionyl chloride (under a nitrogen atmosphere) was stirred at ambient temperature for ten minutes. After the addition of 50 ml of 20% hexane in ether solution, the new mixture was cooled in ice for 30 minutes to precipitate the crude intermediate sulfinyl chloride. The solid was filtered and washed with hexane to yield 3.0 g (63% crude yield) of 3-(chlorosulfinyl)-5-methoxy-1-phenyl-1H-indole-2-carboxylic acid, methyl ester.

The total crude intermediate described above (3.0 g; 0.0087 mole) was dissolved (under a nitrogen atmosphere) in 100 ml of tetrahydrofuran and cooled to −70° C. After dropwise addition of 15.0 ml (0.015 mole) of methyl magnesium bromide (1.0M in ether), the new mixture was stirred at −70° C. for 15 minutes, then quenched by the careful addition of 10.0 ml of 10% aqueous hydrochloric acid. The product was extracted with ether, and the combined organic layers were washed several times with brine and dried (anhydrous magnesium sulfate). Evaporation of the ether solution yielded an oil which was subjected to flash chromatography (silica gel, 50% ethyl acetate/chloroform elution) to yield 2.7 g (57% yield) of the analytically pure methylsulfinyl indole product, mp 140°–144° C.

By variation of the Grignard reagent employed in the second part of the above procedure, also prepared were:

5-Methoxy-3-[(1-methylethyl)sulfinyl]-1-phenyl-1H-indole-2-carboxylic acid, methyl ester), mp 103°–104° C.;

and

5-Methoxy-1-phenyl-3-(phenylsulfinyl)-1H-indole-2-carboxylic acid, methyl ester, mp 146°–148° C.

EXAMPLE 38

5-Methoxy-3-(methylthio)-1-phenyl-1H-indole-2-carboxylic acid

A mixture of 8.0 g (0.023 mole) of 5-methoxy-3-(methylsulfinyl)-1-phenyl-1H-indole-2-carboxylic acid, methyl ester and 10.0 g (0.067 mole) of sodium iodide in 200 ml of acetone (under a nitrogen atmosphere) was maintained at 0°–5° C. and treated dropwise with 10.0 ml (14.9 g; 0.071 mole) of trifluoroacetic anydride. The reaction mixture was stirred for ten minutes, then poured into 300 ml of ice/5% sodium bicarbonate solution. The product was extracted with ether, and the combined extracts were washed with 5% aqueous sodium thiosulfate solution, followed by brine. The organic layer was dried (anhydrous magnesium sulfate) and evaporated to yield 7.5 g (100% yield) of crude intermediate 5-methoxy-3-(methylthio)-1-phenyl-1H-indole-2-carboxylic acid, methyl ester as an oil.

The total crude intermediate ester described above (7.5 g, 0.023 mole) was dissolved in 200 ml of methanol and treated with 55.0 ml (0.11 mole) of 2.0N aqueous sodium hydroxide solution. The mixture was stirred at 60° for 2.5 hours, cooled, and added to 500 g ice/water. Acidification with 10% hydrochloric acid followed by filtration and washing with water yielded 5.0 g (67% yield) of the analytically pure carboxylic acid product, mp 161°–163° C. (dec.).

Similarly prepared by the above procedures from the appropriate sulfinyl esters were:

5-Methoxy-1-phenyl-3-(phenylthio)-1H-indole-2-carboxylic acid, mp 153°–156° C. and 5-Methoxy-3-[(1-methylethyl)thio]-1-phenyl-1H-indole-2-carboxylic acid and
5-Methoxy-3-[(1-methylethyl)thio]-1-phemylmethyl-1H-indole-2-carboxylic acid;
the latter two compounds were non-crystalline and were converted to the carbamoyltetrazoles without extensive purification.

EXAMPLE 39

5-Methoxy-3-(methylthio)-1-phenyl-N-1H-tetrazol-5-yl-1H-indole-2-carboxamide

A mixture of 1.2 g (0.0038 mole) of 5-methoxy-3-(methylthio)-1-phenyl-1H-indole-2-carboxylic acid and 0.74 g (0.0046 mole) of 1,1'-carbonylbis (1H-imidazole) in 50 ml of acetonitrile was stirred at 50° C. under a nitrogen atmosphere for one hour. The reaction mixture was cooled slightly and treated with a mixture of 0.40 g (0.0047 mole) of anhydrous 5-aminotetrazole and 1.1 ml (0.80 g; 0.0079 mole) of triethylamine in 25 ml of warm acetonitrile. The new mixture was then stirred at 50° for 16 hours, cooled, and added to 200 g of ice/H$_2$O. Acidification to pH 4 with acetic acid precipitated the crude product, which was filtered and washed with water. Recrystallization from 30% acetonitrile in 2-propanol yielded 0.92 g (64% yield) of analytically pure carbamoyltetrazole product, mp 252°–253° C.

Similarly prepared by the above procedure from the appropriate carboxylic acid were:
5-Methoxy-3-[(1-methylethyl)thio]-1-phenyl-N-1H-tetrazol-5-yl-1H-indole-2-carboxamide mp 247°–250° C. (dec.);
5-Methoxy-3-[(1-methylethyl)thio]-1-phenylmethyl-N-1H-tetrazol-5-yl-1H-indole-2-carboxamide mp 254°–256° C. (dec.) and
5-Methoxy-1-phenyl-3-(phenylthio)-N-1H-tetrazol-5-yl-1H-indole-2-carboxamide, mp 243°–245° C. (dec.).

EXAMPLE 40

5-Methoxy-3-(methylsulfonyl)-1-phenyl-N-1H-tetrazol-5-yl-1H-indole-2-carboxamide A solution of 1.2 g (0.0032 mole) of 5-methoxy-3-(methylthio)-1-phenyl-N-1H-tetrazol-5-yl-1H-indole-2-carboxamide in 75 ml of water containing 0.27 g (0.0032 mole) of sodium bicarbonate was treated with a slurry of 2.0 g (0.013 mole) of potassium permanganate in 75 ml of acetone. After stirring at ambient temperature for two hours, the mixture was filtered through a bed of Celite filter-aid. The filtrate was cooled in ice and acidified to pH 4 with acetic acid to precipitate the crude sulfone product. The solid was filtered, washed with water, and recrystallized from 2-propanol/acetonitrile/water (10/20/1) to yield 0.38 g (28% yield) of the analytically pure sulfone product, mp 263° C. dec.

EXAMPLE 41

5-Methoxy-3-[(1-methylethyl)sulfonyl]-1-phenyl-1H-indole-2-carboxylic acid

A solution of 3.0 g (0.0081 mole) of 5-methoxy-3-[(1-methylethyl)sulfinyl]-1-phenyl-1H-indole-2-carboxylic acid, methyl ester in 250 ml of acetone was treated with a slurry of 2.6 g (0.016 mole) of potassium permanganate in 50 ml of water. After stirring at ambient temperature for four hours, the excess oxidant was destroyed by the addition of solid potassium iodide. The reaction mixture was filtered through a bed of Celite filter-aid, and a volume of water equivalent to that of the filtrate was added. The precipitated solid was filtered and washed with water to yield 1.2 g (40% yield) of intermediate sulfone 5-methoxy-3-[1-methylethyl)sulfonyl]-1-phenyl-1H-indole-2-carboxylic acid, methyl ester, mp 164°–166° C.

A 1.0 g (0.0026 mole) sample of the above sulfone ester was saponified with sodium hydroxide as described in Example 38 to yield 0.75 g (77% yield) of the corresponding sulfone carboxylic acid, mp 171°–173° C.

EXAMPLE 42

5-Methoxy-3-[(1-methylethyl)sulfinyl]-1-phenylmethyl-1H-indole-2-carboxylic acid, ethyl ester A suspension of 7.0 g (0.023 mole) of 5-methoxy-1-phenylmethyl-1H-indole-2-carboxylic acid, ethyl ester (Y. Murakami, et al, *Synthesis*, 738 (1984)) in 75 ml of n-heptane under an argon atmosphere was cooled in ice and treated with 15.0 ml (24.5 g; 0.21 mole) of thionyl chloride. The mixture was stirred for 30 minutes, and the precipitated sulfinyl chloride intermediate was filtered and washed several times with hexane to yield 7.3 g (76% yield) of 3-(chlorosulfinyl)-5-methoxy-1-phenylmethyl-1H-indole-2-carboxylic acid, ethyl ester.

The total crude intermediate described above was treated with isopropylmagnesium bromide in a manner analogous to that described in Example 37. Flash chromatographic purification (silica gel, 10% ethyl acetate in hexane elution) of the initial oil product yielded 4.2 g (46% yield) of the analytically pure (1-methylethyl)sulfinyl indole ester product, mp 97°–99° C.

EXAMPLE 43

3-(Diethylamino)-5-methoxy-1-phenyl-1H-indole-2-carboxylic acid

A mixture of 2.4 g (0.0066 mole) of 3-(diethylamino)-5-methoxy-1-phenyl-1H-indole-2-carboxylic acid, ethyl ester (prepared as described in Example 34), and 1.6 g (0.040 mole) of sodium hydroxide in 50 ml of ethanol plus 15 ml of water was stirred at 65° for four hours. The reaction mixture was cooled, added to 250 g ice/brine, and acidified to pH 2 with dilute hydrochloric acid. The product was extracted with ether, and the combined organic layers were washed twice with brine and dried (anhydrous magnesium sulfate). Evaporation of the ether solution left a solid residue, which was triturated with ether/hexane to yield 1.55 g (70% yield) of the crude acid product. A sample recrystallized from ether/hexane was analytically pure, mp 141°–143° C.

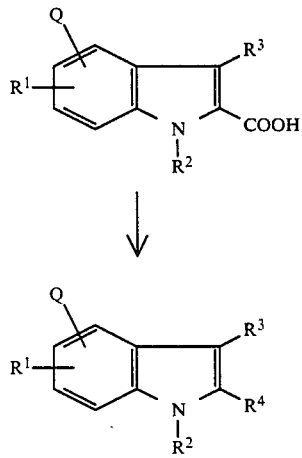

SCHEME I

SCHEME II
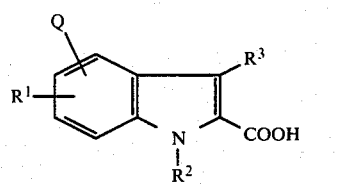
III
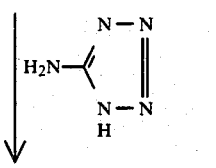
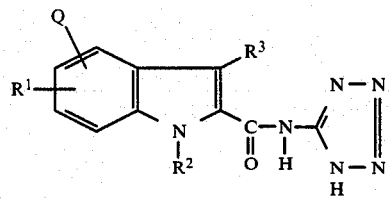
I₁
SCHEME III
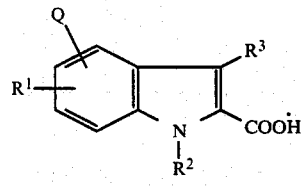
III
Step I ↓ (1) H₂NR
       (2) —H₂O
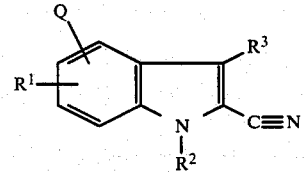
IV
Step II ↓
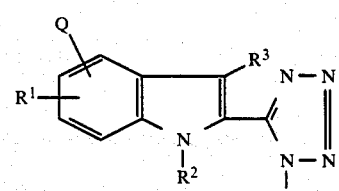
I₂
SCHEME IV
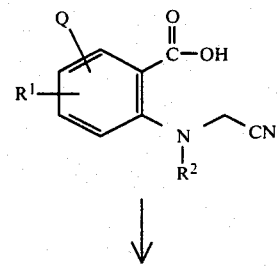
VII
↓
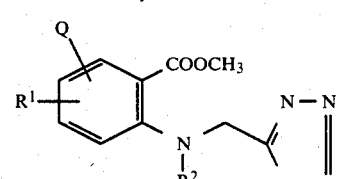
VI
↓ Protecting agent
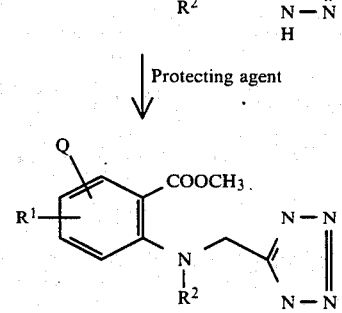
V
↓
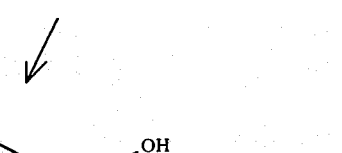 →Hal R⁶
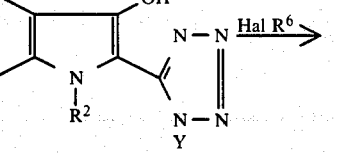
I₃
SCHEME V
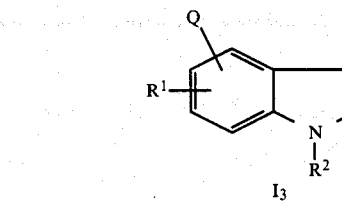
VIII
↓ (CH₃)₂SO₄
  K₂CO₃

-continued
SCHEME V
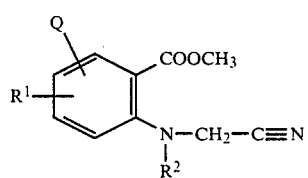
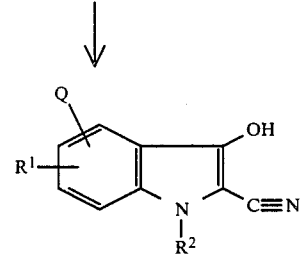 IV
SCHEME VI
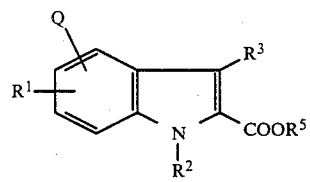 IX
(1) KOH; (2) H⁺
or
(1) KO—⧌—, DMSO; (2) H⁺
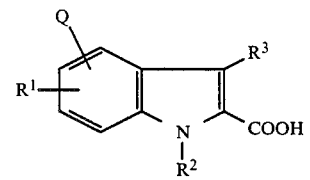 III
SCHEME VII
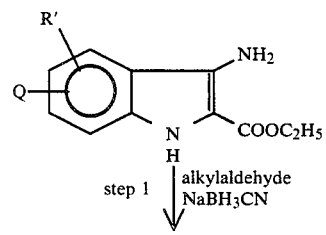 XX
step 1 | alkylaldehyde
NaBH₃CN
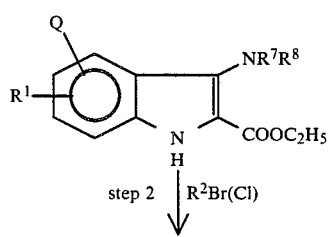 XXI
step 2 | R²Br(Cl)
-continued
SCHEME VII
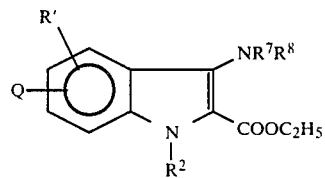 IX₁
SCHEME VIII
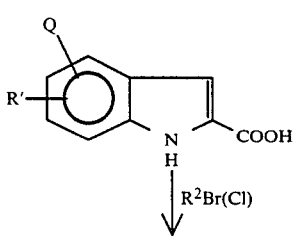 XXX
R²Br(Cl)
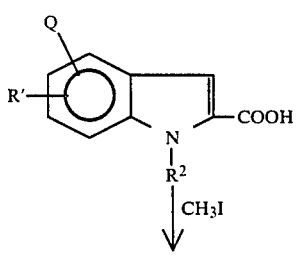 XXXI
CH₃I
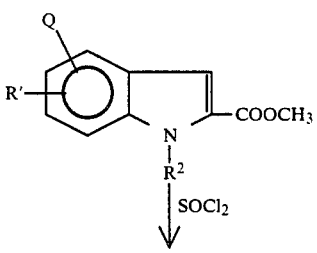 XXXII
SOCl₂
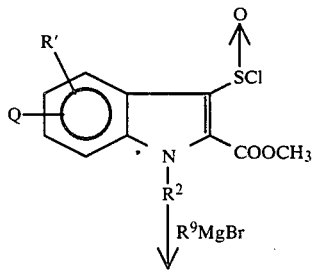 XXXIII
R⁹MgBr
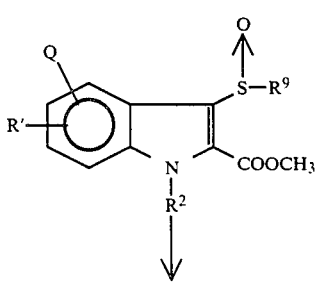 XXXIV

-continued
SCHEME VIII

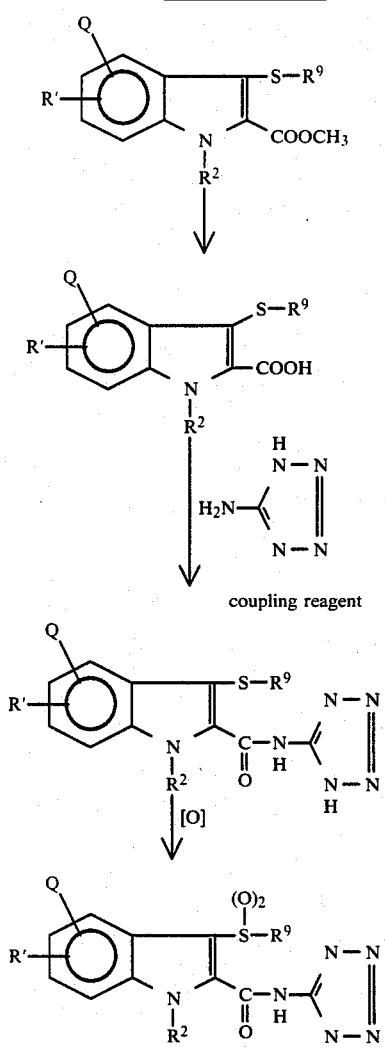

coupling reagent

FORMULA I

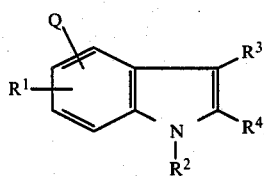

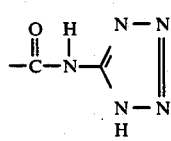 A

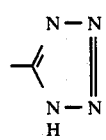 B

-continued
FORMULA I¹

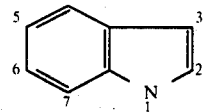

IX₂

IX₃

We claim:
1. A compound having the formula

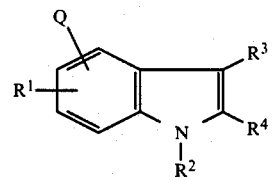 I wherein (1) R¹ and Q are independently H, alkyl of from one to twelve carbons, alkoxy of from one to twelve carbons, mercapto, alkylthio of from one to four carbons, alkylsulfinyl of from one to four carbons, alkylsulfonyl of from one to four carbon, hydroxy, R¹ taken twice having each on adjacent carbons such that the two R¹s together are methylenedioxy, nitro, amino, mono- or di-alkyl amino wherein the alkyl is of from one to four carbons, or halogen: (2) R² is H, alkyl of from one to twelve carbons, phenyl, substituted phenyl, having at least one substituent selected from alkyl of from one to four carbons, alkoxy of from one to four carbons, hydroxy, nitro, amino, mono- di-alkyl amino wherein the alkyl is of from one to four carbons, mercapto, alkylthio of from one to four carbons, methylenedioxy, or halogen, or benzyl; (3) R³ is H, alkyl of from one to twelve carbons, alkoxy of from one to twelve carbons, mercapto, alkylthio of from one to four carbons, phenylthio, substituted phenylthio having at least one substituent selected from alkyl of from one to four carbons, alkoxy of form one to four carbons, hydroxy, nitro, amino, mono- or di-alkyl amino wherein the alkyl is from one to four carbons, mercapto, alkylthio of from one to four carbons, methylenedioxy, or halogen, alkylsulfinyl of from one to four carbons, phenylsulfinyl, substituted phenylsulfinyl having at least one substituent selected from alkyl of from one to four carbons, alkoxy of from one to four carbons, hydroxy, nitro, amino, mono- or di-alkyl amino, mercapto, alkylthio of from one to four carbons, methylenedioxy, or halogen, alkylsulfonyl of from one to four carbons, inclusive, phenylsulfonyl, substituted phenylsulfonyl having at least one substituent selected from alkyl of from one to four carbons, alkoxy of from one to four carbons, hydroxy, nitro, amino, mono- or di-alkyl amino wherein the alkyl is of from one to four carbons, mercapto, alkylthio of from one to four carbons, methylenedioxy, or halogen, amino, mono- or di-alkyl amino wherein the alkyl is of from one to four carbons; and (4) R⁴ is

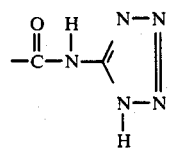 A

-continued

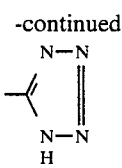 B with the proviso that for R¹, Q and R³ mixed oxidation states of sulfur are not present; and pharmaceutically acceptable salts thereof.

2. A compound according to claim 1 wherein R⁴ is

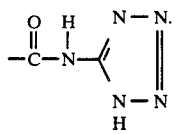 A

3. A compound according to claim 1 wherein R⁴ is

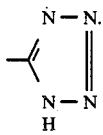 B

4. A compound according to claim 2 wherein R³ is alkoxy.

5. A compound according to claim 4 wherein the specific embodiment is 3-methoxy-1-methyl-N-1H-tetrazol-5-yl-1H-indole-2-carboxamide.

6. A compound according to claim 4 wherein the specific embodiment is 1-hexyl-3-methoxy-N-1H-tetrazol-5-yl-1H-indole-2-carboxamide.

7. A compound according to claim 4 wherein the specific embodiment is 3-methoxy-1-nonyl-N-1H-tetrazol-5-yl-1H-indole-2-carboxamide.

8. A compound according to claim 4 wherein the specific embodiment is 3-methoxy-1-(phenylmethyl)-1N-1H-tetrazol-5-yl-1H-indole-2-carboxamide.

9. A compound according to claim 4 wherein the specific embodiment is 3-methoxy-1-phenyl-N-1H-tetrazol-5-yl-1H-indole-2-carboxamide.

10. A compound according to claim 4 wherein the specific embodiment is 1-phenyl-3-(phenylmethoxy)-N-1H-tetrazol-5-yl-1H-indole-2-carboxamide.

11. A compound according to claim 4 wherein the specific embodiment is 3-(1-methylethoxy)-1-phenyl-N-1H-tetrazol-5-yl-1H-indole-2-carboxamide.

12. A compound according to claim 4 wherein the specific embodiment is 1-(4-methoxyphenyl)-3-(1-methylethoxy)-N-1H-tetrazol-5-yl-1H-indole-2-carboxamide.

13. A compound according to claim 4 wherein the specific embodiment is 5-chloro-3-(1-methylethoxy)-1-phenyl-N-1H-tetrazol-5-yl-1H-indole-2-carboxamide.

14. A compound according to claim 4 wherein the specific embodiment is 5-methoxy-1-methyl-3-(1-methylethoxy)-N-1H-tetrazol-5-yl-1H-indole-2-carboxamide.

15. A compound according to claim 4 wherein the specific embodiment is 3,5-dimethoxy-1-phenyl-N-1H-tetrazol-5-yl-1H-indole-2-carboxamide.

16. A compound according to claim 4 wherein the specific embodiment is 3-ethoxy-5-methoxy-1-phenyl-N-1H-tetrazol-5-yl-1H-indole-2-carboxamide.

17. A compound according to claim 4 wherein the specific embodiment is 5-methoxy-1-phenyl-3-(phenylmethoxy)-N-1H-tetrazol-5-yl-1H-indole-2-carboxamide.

18. A compound according to claim 4 wherein the specific embodiment is 5-methoxy-3-(1-methylethoxy)-1-phenyl-N-1H-tetrazole-5-yl-1H-indole-2-carboxamide.

19. A compound according to claim 4 wherein the specific embodiment is 3-methoxy-N-1H-tetrazol-5-yl-1H-indole-2-carboxamide, 3-methoxy-1-nonyl-N-1H-tetrazole-5-yl-1H-indole-2-carboxamide, 5-methoxy-3-(n-nonyloxy)-1-phenyl-N-1H-tetrazol-5-yl-1H-indole-2-carboxamide, or 3-(n-dodecyloxy)-5-methoxy-1-phenyl-N-1H-tetrazol-5-yl-1H-indole-2-carboxamide.

20. A compound according to claim 2 wherein the specific embodiment is 3-(diethylamino)-5-methoxy-1-phenyl-N-1H-tetrazol-5yl-1H-indole-2-carboxamide.

21. A compound according to claim 2 wherein the specific embodiment is 5-methoxy-3-(methylthio)-1-phenyl-N-1H-tetrazol-5-yl-1H-indole-2-carboxamide.

22. A compound according to claim 2 wherein the specific embodiment is 5-methoxy-3-[1-methylethyl)thio]-1-phenyl-N-1H-tetrazol-5-yl-1H-indole-2-carboxamide.

23. A compound according to claim 2 wherein the specific embodiment is 5-methoxy-1-phenyl-3-(phenylthio)-N-1H-tetrazol-5-yl-1H-indole-2-carboxamide.

24. A compound according to claim 2 wherein the specific embodiment is 5-methoxy-3-(methylsulfony)-1-phenyl-N-1H-tetrazol-5-yl-1H-indole-2-carboxamide.

25. A compound according to claim 2 wherein the specific embodiment is 5-methoxy-3-[(1-methylethyl)-thio]-1-phenylmethyl-N-1H-tetrazol-5-yl-1H-indole-2-carboxamide.

26. A pharmaceutical composition comprising an effective amount of a compound according to claim 1 in admixture with a pharmaceutically acceptable carrier.

27. A method of treating allergies in mammals which comprises administering to such mammal in need thereof an effective amount of a pharmaceutical composition according to claim 26.

28. A compound according to claim 18 wherein the specific embodiment is 5-methoxy-3-(1-methylethoxy)-1-phenyl-N-1H-tetrazol-5-yl-1H-indole-2-carboxamide L-arginate salt.

29. A compound of claim 4 wherein Q is hydrogen.

* * * * *

UNITED STATES PATENT AND TRADEMARK OFFICE
CERTIFICATE OF CORRECTION

PATENT NO. : 4,675,332

DATED : June 23, 1987

INVENTOR(S) : David T. Connor, Paul C. Unangst, S. Russell Stabler

It is certified that error appears in the above-identified patent and that said Letters Patent is hereby corrected as shown below:

Column 26, line 33 after "mono-" add --or--.

Column 26, line 69 add --or--.

Signed and Sealed this

Twenty-sixth Day of January, 1988

Attest:

DONALD J. QUIGG

Attesting Officer

Commissioner of Patents and Trademarks